United States Patent
Iwasaki

(10) Patent No.: US 6,593,583 B2
(45) Date of Patent: Jul. 15, 2003

(54) ION BEAM PROCESSING POSITION CORRECTION METHOD

(75) Inventor: Kouji Iwasaki, Chiba (JP)

(73) Assignee: Seiko Instruments Inc. (JP)

( * ) Notice: Subject to any disclaimer, the term of this patent is extended or adjusted under 35 U.S.C. 154(b) by 94 days.

(21) Appl. No.: 09/754,649

(22) Filed: Mar. 22, 2001

(65) Prior Publication Data
US 2001/0032936 A1 Oct. 25, 2001

(30) Foreign Application Priority Data
Jan. 11, 2000 (JP) ........................... 2000-006122

(51) Int. Cl.$^7$ .................... H01J 37/08; G21G 5/00; G21K 5/10; G21K 7/00; G01N 23/00
(52) U.S. Cl. ............... 250/492.1; 250/492.2; 250/492.21; 250/492.23; 250/492.3; 250/306; 250/307; 250/309
(58) Field of Search .............. 430/5; 250/491.1, 250/41.9, 492.1, 492.2, 492.21, 492.23, 492.3, 306, 307, 309

(56) References Cited

U.S. PATENT DOCUMENTS

| | | | | |
|---|---|---|---|---|
| 3,686,499 A | * | 8/1972 | Omura et al. | |
| 4,868,068 A | * | 9/1989 | Yamaguchi et al. | |
| 4,933,565 A | * | 6/1990 | Yamaguchi et al. | 250/492.2 |
| 5,113,072 A | * | 5/1992 | Yamaguchi et al. | 250/309 |
| 5,134,298 A | * | 7/1992 | Inagaki et al. | 250/491.1 |
| 5,472,507 A | * | 12/1995 | Yamaguchi et al. | |
| 5,497,034 A | * | 3/1996 | Yamaguchi et al. | |
| 5,800,949 A | * | 9/1998 | Edo et al. | |
| 5,824,598 A | * | 10/1998 | Yamaguchi et al. | |
| 5,952,658 A | * | 9/1999 | Shimase et al. | 250/309 |
| 2001/0032936 A1 | * | 10/2001 | Iwasaki | 250/491.1 |
| 2002/0122992 A1 | * | 9/2002 | Kanamitsu | |

FOREIGN PATENT DOCUMENTS

JP         63-305358    * 12/1988    ............ G03F/1/00

* cited by examiner

Primary Examiner—John R. Lee
Assistant Examiner—Bernard E. Souw
(74) Attorney, Agent, or Firm—Adams & Wilks

(57) ABSTRACT

The present invention provides a focused ion beam method in which positional correction is performed with reference to reference points on a sample and for carrying out processing using an ion beam, in which reference point conformation does not take up a lot of time, and which is capable of accurate fine processing. The present invention performs high precision processing with correction performed at short intervals using reference mark confirmation when fine processing requiring accuracy is performed, while positional correction is carried out at long intervals when accuracy is not required, which means there is no wasted time because inefficient correction processing is omitted.

9 Claims, 3 Drawing Sheets

ION BEAM PROCESSING POSITION CORRECTION METHOD

BACKGROUND OF THE INVENTION

The present invention relates to a position correction method carried out in order to realize accurate processing, in processing such as photomask processing used in the manufacture of semiconductor devices using a focused ion beam apparatus, namely a point drift correction method.

When executing a method in which a focused ion beam is irradiated to repeatedly scan over a specified region on a sample surface having a patterned film formed on a substrate surface, the patterned film formed on a substrate surface, the patterned film is removed by etching, and organic compound vapor is sprayed on a specified pattern processing region on the substrate using a gas gun together with forming a patterned film by irradiating an ion beam, accurate positioning of the irradiating ion beam with respect to the sample is necessary. However, when carrying out fine processing using a focused ion beam, problems arise such as the stability of a stage etc. for mounting an ion beam optical system and the sample, and positional drift of the ion beam irradiated on the sample due to variations in environmental conditions such as potential difference and temperature of the sample surface. Conventionally, in order to perform accurate processing, a method has been used in which a pattern suitable for the sample surface is registered and stored as a reference pattern. The reference pattern is then detected at regular intervals during processing and when there is driving from a stored position processing is carried out to correct this positional drift.

The main components of a focused ion beam apparatus performing this ion beam processing are shown in FIG. 5. An ion beam focused through an ion optical system, not shown in the drawing, is suitably deflected by a scanning electrode 1 and irradiated onto a surface of a sample 2 mounted on a sample stage 3. If the ion beam is irradiated onto the sample surface, secondary charged particles are ejected from the sample surface, the nature of the secondary charged particles depending on the sample material at sections irradiated with the ion beam. Secondary charged particles ejected by the irradiating beam are captured by the detector 4 and an amount of charged particles is detected. This value is digitized by the A/D converter 6, and stored in a storage section of the computer 8 as data pertaining to locations subjected to beam irradiation. If the computer designates beam scanning for a specified region, a deflection voltage is applied to the scanning electrode 1 so as to scan the region, via the drive system 7. Detection values of secondary charged particles for each beam spot are stored together with positional information, based on this scanning, to obtain a scanned image of the region designated by the computer 8, thus making it possible to display images as required on the display 10. An operation for removing a patterned film by etching irradiates the processing region with a beam as a result of the computer 8 applying a suitable deflection voltage to the scanning electrode 1 through the drive system 7, based on settings made via the operating section 9. Also, processing for forming the patterned film on the substrate involves the computer executing processing to spray organic compound vapor onto a specified pattern processing region using a gas gun 5 through the drive system 7, and applying a suitable deflection voltage via the drive system 7 to irradiate the specified region with an ion beam, based on settings made via the operating section 9. This type of ion beam processing apparatus performs processing in the above described operation, and also executes operations to acquire the scanned image repeatedly during processing, detect where the reference pattern drifts form the initial position and corrects this drift, so that positional drift does not arise.

Japanese Patent Laid-open No. Hei. 5-4660 discloses a method of performing spot processing using an ion beam and using these spots as basic reference points, in order to improve recognition accuracy of a sample without a suitable reference pattern and a reference pattern. Specifically, as shown in FIG. 4, secondary charged particles are knocked off while scanning a focused ion beam to display a sample surface image. A reference mark (start time) $M_0$ is stored as a position on the image. After scanning a specified number of tomes by limiting a scanning range of the ion beam for the processing operation, a scan image is acquired again, a reference mark (correction time) $M_i$ is detected, an amount of slippage of the reference mark is obtained by comparing with the reference mark position $M_0$ being stored, and finally the beam position recognition is corrected based on this amount of slippage (amount of movement).

A description will now be given of an operation in conventional ion beam processing, for cross sectional observation of a semiconductor element shown in FIG. 4. If the place where it is desired to carry out cross sectional observation of the sample (the finishing processing region in the drawing) is specified, then first of all a reference mark M is etched at a position a suitable distance from the desired location, a protection film is deposited over an area close to the cross section to be observed, large holes are formed in a forward section of the part to be observed, the large holes are made wider, and finally finishing processing is performed to polish the section to be observed. Precise processing is possible as long as the positional relationship between the sample and the ion beam at this time is kept constant, but as has already been mentioned, microscopic positional variations occur during processing. Accordingly, positional correction is carried out in a computer 8 by detecting the slippage by interrupting processing to obtain a scan image and then comparing the reference mark $M_i$ with the initial image position $M_0$, and correcting a voltage applied to a scanning electrode. If the amount of positional correction is large, correction is performed by moving the sample stage 3, but generally speaking drift that occurs during processing is extremely small, and correction is performed by adjusting the scanning electrode. In the related art, this positional correction is generally carried out at fixed intervals, as shown in FIG. 3. In order to carry out accurate processing it is necessary to frequently confirm the position of the reference mark (reference point) M, but if such actions are carried out frequently the amount of time spent on the image processing is increased, and overall processing time becomes long. Shortening the processing time and improving accuracy are therefore mutually incompatible.

The present invention aims to solve the above described problems, and provides a focused ion beam processing method for promoting processing that is capable of very accurate finishing processing without the need for a substantial amount of time for confirming reference points.

SUMMARY OF THE INVENTION

The present invention realizes high precision focused ion beam processing in a comparatively short time, with no wasted time, by carrying out positional correction using reference mark confirmation at short time intervals when performing fine processing that requires high accuracy, but carrying out positional correction at long time intervals when performing processing that does not require high accuracy, thus doing away with inefficient positional correction.

DETAILED DESCRIPTION OF THE PREFERRED EMBODIMENT

Figure 2:
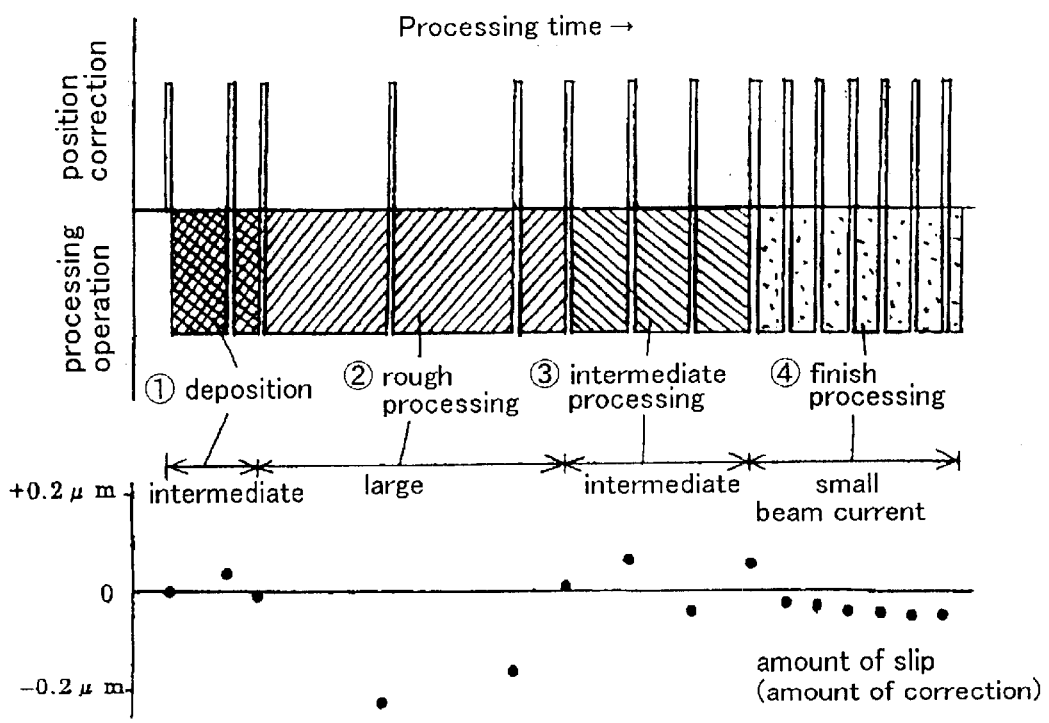
FIG. 2 is a view illustrating the basic operation of the present invention.
Figure 3:
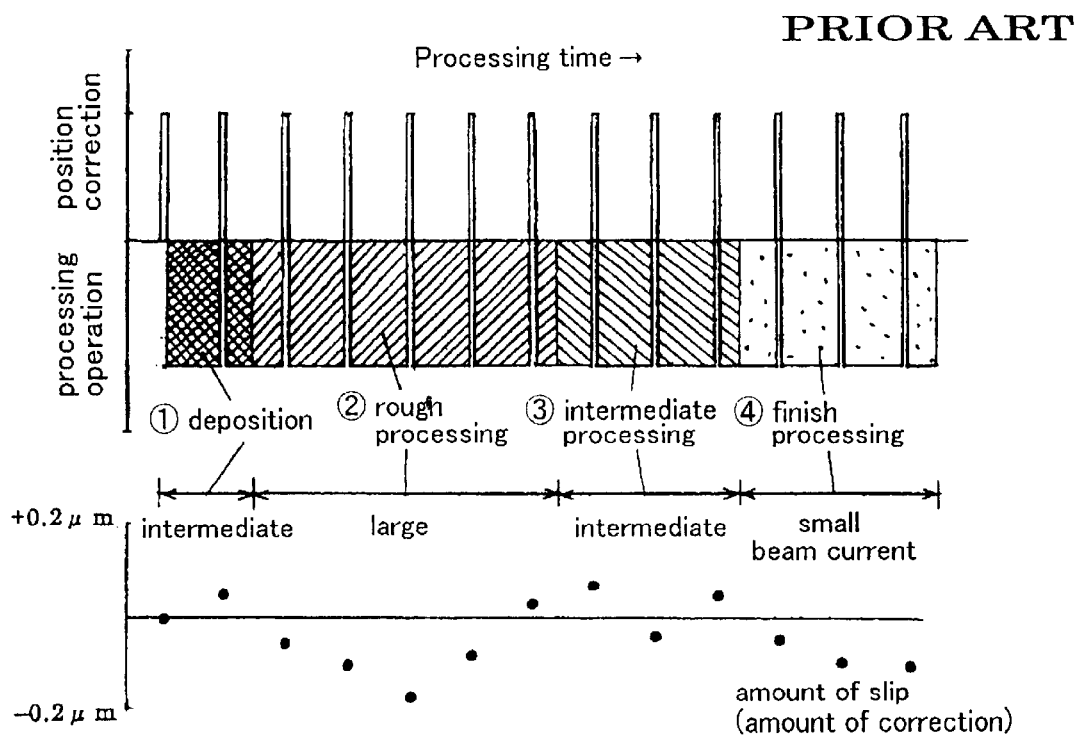
FIG. 3 is a view illustrating the operation of a related art method.
Figure 4:
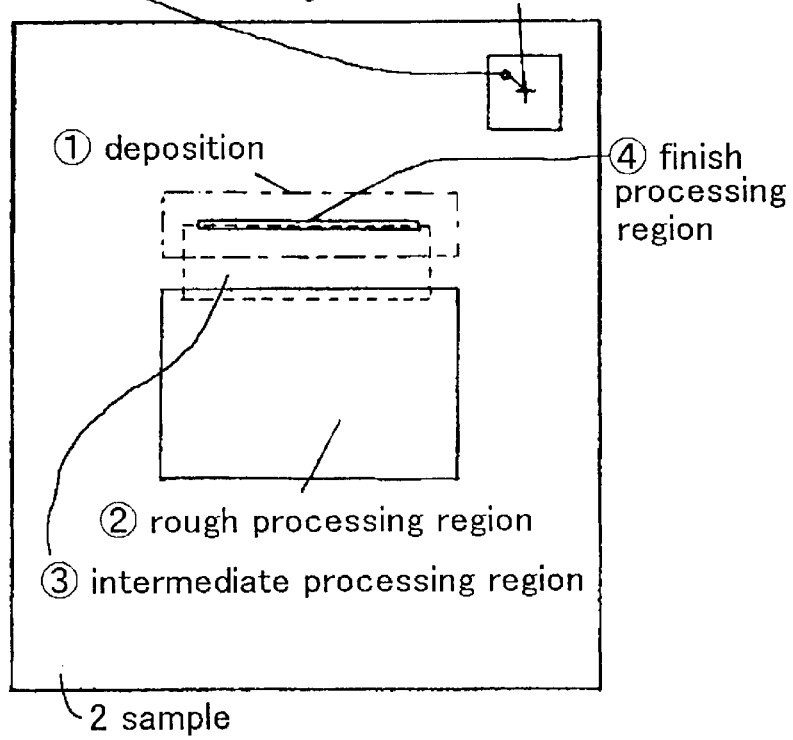
FIG. 4 is a view illustrating focused ion beam processing and positional correction.
Figure 5:
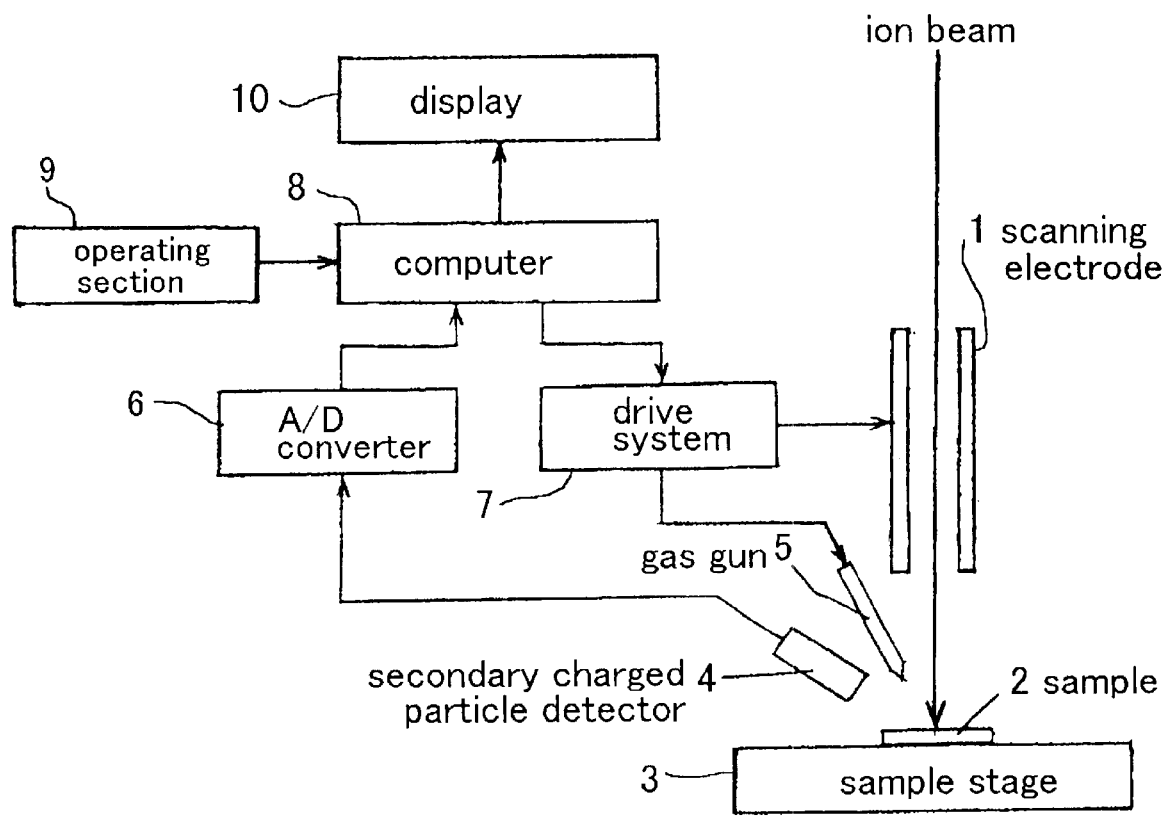
FIG. 5 is a block diagram showing essential elements of a focussed ion beam apparatus.

The present invention takes into consideration maintenance of processing accuracy when carrying out positional correction at fixed intervals, and the fact that performing positional correction in a short time when effective processing is required is actually something of a compromise and not a complete solution, and enables effective processing not at fixed time intervals, but at time intervals according to actual operation content. In order to achieve this, in a manufacturing procedure, it is preferable that in rough processing a sample is easily tilted, and holes are formed to make it possible to irradiate an ion beam from a steep angle with respect to an observed surface. However, fine processing is not required. Accordingly, this operation has rough processing performed with a large beam current without paying attention to the accuracy of sample processing, and positional drift is not a problem with this processing. Positional correction during this operation can be therefore carried out less frequently, thus reducing wasted time. Positional correction at the time of deposition or intermediate processing is carried out at an intermediate timing, and since finishing processing requires accurate processing, positional correction is carried out more frequently at that stage. This method of operation is shown in FIG. 2. In this embodiment, reference numeral 2 represents correction timing during rough processing, reference numeral 3 represents intermediate processing and 1 represents deposition, and reference numeral 4 represents finish processing. Rough processing is performed with a large beam diameter, the beam diameter at the time of intermediate processing and deposition is intermediate, and finish processing is performed accurately with a fine beam diameter, but this beam diameter depends on the beam current. The timing at which this correction processing is carried out is set in a computer 8 according to operation content, and initialization correction is carried out when the ion beam apparatus is started up or during switching processes. On all subsequent occasions positional correction is performed at a timing interval that depends on processing content, in other words, at intervals that depend on the beam diameter.

The present invention carries out positional correction not at constant intervals, but at intervals depending on the operation being performed, as shown in FIG. 2. Specifically, when accurate processing is required, positional correction is carried out frequently, while when performing rough processing that does not require accuracy the operation continues with a reduced frequency of performing positional correction, to thereby perform accurate processing that requires comparatively less processing time. As well as changing the timing of positional correction depending on the operation, the present invention can also vary the timing at which positional correction is carried out, by, after establishing an initial correction value, adding a correction amount each time at short intervals when the amount of correction is large or at long intervals when an amount of correction is small, to thereby perform correction even more efficiently.

Embodiment

Figure 1:
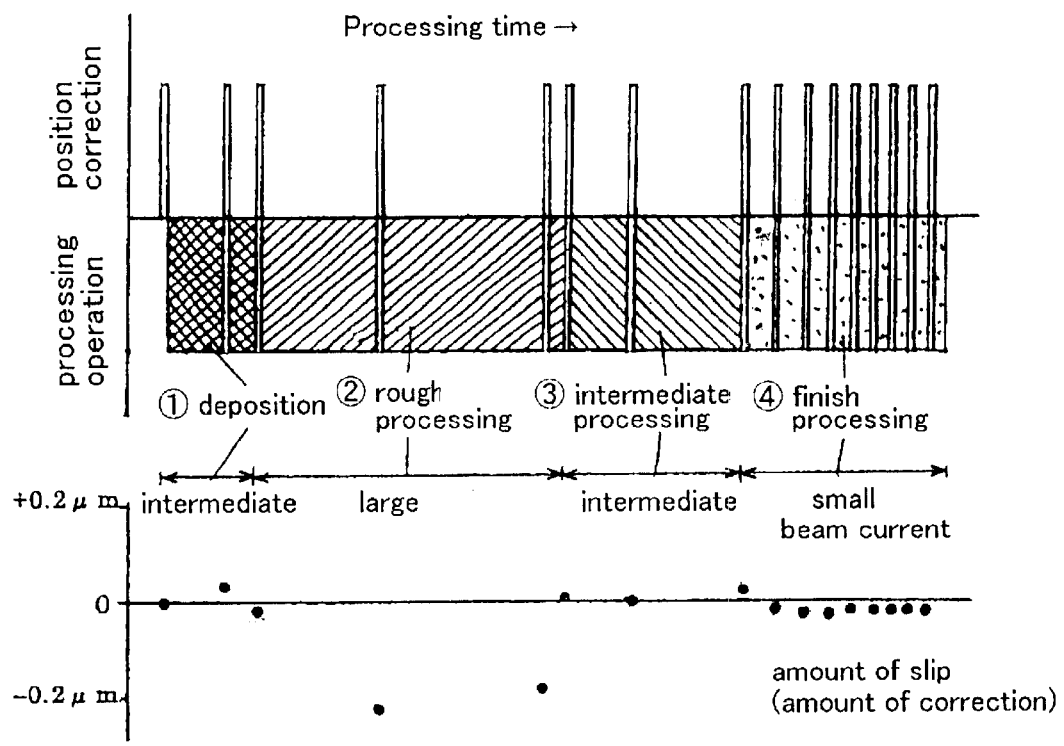
FIG. 1 is a view illustrating the operation of an embodiment of the present invention.

A first embodiment of the present invention will now be described with reference to FIG. 1.

This embodiment basically changes the timing at which positional correction is carried out according to the processing content, but a positional correction timing interval does not simply depend on the processing content. An initial timing is determined at an interval set according to the processing content, but after that the positional correction is changed by adding a detected slippage amount to a timing interval set according to the processing content.

A beam current at the time of rough processing is a heavy current of from a few nA to a few tens of nA, and the beam diameter is about Ø0.5 μm, the beam current during intermediate processing or deposition is an intermediate current of a few hundred pA, with a beam diameter in this case being about Ø05 μm, and the beam current during finishing processing is a small current of a few tens of pA, with a beam diameter in this case being about. Ø02 μm.

In this embodiment, a positional correction timing is initialized at start up and when switching processing depending on the diameter of the ion beam used (depending on an ion current value), and specifically is set to 1 minute for finishing processing, 2 minutes for deposition and intermediate processing, and 4 minutes for rough processing.

Then, the time of the next positional correction $T_i$, is corrected using the following equation so that a correction value of a correction interval $T_{i-1}$ at that time is reduced when the ion beam diameter is comparatively large or lengthened when it is comparatively small. However, maximum and minimum values are set for respective time intervals T so that they do not deviate substantially from the initial value.

$$T_i = T_{i-1} \times 2/(1 + |\text{previous correction amount/beam diameter}|) \quad \text{Equation 1}$$

A number of times of correction and correction amount for this embodiment are shown in table 1 below. Once the observation surface position on a sample is determined, a protective film is deposited around the periphery.

This operation is performed with an intermediate current, so an initial correction timing value $2T_0$ is double a finishing processing time $T_0$. Specifically, as it is $T_0=1$ minute in this embodiment, the value is set in 2 minutes.

TABLE 1

| processing content | number of time of correction | amount of correction μm | correction time interval min |
|---|---|---|---|
| start | 0 | 0 | $2T_0 = 2.$ |
| deposition | 1 | +0.04 | $2T_0 \times 1.11 = 2.22$ |
| switching of processes | 2 | −0.01 | $4T_0 = 4$ |

TABLE 1-continued

| processing content | number of time of correction | amount of correction μm | correction time interval min |
|---|---|---|---|
| rough processing | 3 | −0.24 | $4T_0 \times 1.35 = 5.40$ |
| switching of processes | 4 | −0.17 | $4T_0 \times 2.01 = 8.04$ |
| switching of processes | 5 | +0.01 | $2T_0 = 2$ |
| intermediate processing | 6 | 0 | $2T_0 \times 2 = 4$ |
| switching of processes | 7 | +0.03 | $T_0 = 1$ |
| finish processing | 8 | −0.02 | $T_0 \times 1 = 1$ |
| the same as the above | 9 | −0.03 | $T_0 \times 0.8 = 0.8$ |
| the same as the above | 10 | −0.03 | $T_0 \times 0.64 = 0.64$ |
| the same as the above | 11 | −0.02 | $T_0 \times 0.64 = 0.64$ |
| the same as the above | 12 | −0.02 | $T_0 \times 0.64 = 0.64$ |
| the same as the above | 13 | −0.02 | $T_0 \times 0.64 = 0.64$ |
| the same as the above | 14 | −0.02 | $T_0 \times 0.64 = 0.64$ |
| the same as the above | 15 | −0.02 | $T_0 \times 0.64 = 0.64$ |

The first time positional correction is performed at $2 T_0=2$ minutes after start up. A drift amount (vector quantity) at this time is +0.04 m so drift correction is performed to that extent, and an interval to the next correction is calculated from equation 1 above to give $2 T_0 \times 2/(1+|0.04/0.05|)=2 T_0 \times 1.11=2.2$ minutes.

Since the initial value 0.04 μm is smaller than the beam diameter of 0.05 μm, correction timing is set to 1.11 times longer than the initially set timing interval.

However, between this correction and subsequent correction the operation of forming the protective film is completed, and there is a period of switching to hole making processing, and so the second position correction is performed when this processing switch takes place.

The amount of drift at this time is −0.01 μm, drift correction to that extent is performed, but, the time for the subsequent positional correction is set to $4T_0=4$ minutes according to the beam diameter at the time of rough processing.

In the third positional correction, the amount of slippage is 0.24 μm, so drift correction is performed to that extent, and an interval to the next correction is calculated from equation 1 above to give $4T_0 \times 2/(1+|0.24/0.5|)=4 T_0 \times 1.35=5.20$ minutes.

Specifically, the fourth positional correction is performed 5.20 minutes after the third positional correction, and the amount of slippage at that time is 0.17 μm, so drift correction is performed to that extent, and an interval to the next correction is calculated from equation 1 above to give $4T_0 \times 1.35 \times 2/(1+|0.17/0.5|)=4T_0 \times 1.35 \times 1.49=8.04$ minutes.

However, before the time interval for the fifth correction expires, there is a switch from rough processing to intermediate processing, so the fifth correction is performed at that time. Drift correction for an amount of drift of +0.01 μm at that point in time is performed, and an interval to the sixth correction is set to $2T_0=2$ minutes according to the beam diameter at the time of intermediate processing.

Then, since the drift amount in the sixth correction is 0, an interval to the next correction is calculated from equation 1 above to give $2T_0 \times 2/(1+|0/0.05|)=2 T_0 \times 2=4$ minutes.

Finishing processing then commences before the time for the seventh correction arrives, and an amount of drift at that time is +0.03 μm.

This value can be used in drift correction, but it is not used in calculating a time interval to the next positional correction, and the eighth correction is carried out at a point in time when $T_0=1$ minute, according to the beam diameter at the time of finishing processing, has expired from the time of the switch.

Since the drift amount at that time is −0.02 μm, drift correction is carried out and an interval to execution of the ninth correction is calculated from equation 1 above to give $T_0 \times 2/(1+|0.02/0.02|)=T_0 \times 1=1$ minute.

In the ninth positional correction, the amount of slippage is −0.03 μm, so drift correction is performed to that extent, and an interval to execution of the tenth positional correction is calculated from equation 1 above to give $T_0 \times 2/(1+|0.03/0.02|)=T_0 0.8=0.8$ minutes.

In the tenth positional correction, the amount of slippage is −0.03 μm, so drift correction is performed to that extent, and an interval to execution of the eleventh positional correction is calculated from equation 1 above to give $T_0 \times 0.8 \times 2/(1+|0.03/0.02|)=T_0 \times 0.64=0.64$ minutes.

In the eleventh positional correction, the amount of slippage is −0.02 μm, so drift correction is performed to that extent, and an interval to execution of the twelfth positional correction is calculated from equation 1 above to give $T_0 \times 0.64 \times 2/(1+|0.02/0.02|)=T_0 \times 0.64=0.64$ minutes.

In the twelfth to fifteenth corrections, the amount of drift is the same as the beam diameter, namely 0.02 μm, so processing is carried out at the same time interval of $T_0 \times 0.64=0.64$ minutes, and before the sixteenth correction finishing processing is completed and the manufacturing process itself is completed.

The present invention is directed to a focused ion beam method in which positional correction is performed with reference to reference points on a sample and for carrying out processing using an ion beam, in which high precision processing is carried out with correction performed at short intervals when fine processing requiring accuracy is performed, while positional correction is carried out at longer intervals when accuracy is not required. There is therefore no wasted time due to the execution of correction processing at long intervals when high accuracy is not required, and it becomes possible to efficiently carry out accurate processing by performing positional correction frequently at short intervals.

Not only is this interval set according to the processing content, it is also possible to perform positional correction at a more efficient timing using feed back control to add a correction amount at the time of correction to the correction contents.

What is claimed is:

1. A focused ion beam processing method, comprising the steps of: using a focused ion beam for processing a sample; and performing position correction of the focused ion beam with reference to at least one reference point on the sample; wherein position correction is repeatedly carried out at short time intervals when high precision processing is being carried out using the focused ion beam and high accuracy beam positioning is required, and position correction is repeatedly carried out at long time intervals when low precision processing is being carried out using the focused ion beam and high accuracy beam positioning is not required.

2. A focused ion beam processing method according to claim 1; wherein the step of using a focused ion beam for processing a sample comprises processing the sample to obtain a cross section thereof by forming a protective film on the sample, forming a hole in the protective film and the sample, polishing the hole, and observing the cross section using the focused ion beam; and the step of performing position correction of the focused ion beam is performed at time intervals determined based on a beam diameter of the focused ion beam, such that during formation of the protective film position correction is carried out at intermediate time intervals, during formation of the hole position correction is carried out at long time intervals, and during polishing of the hole and observing the cross section position correction is carried out at short time intervals.

3. A focused ion beam processing method according to claim 1; further comprising the step of setting initial times for position correction intervals for each beam diameter used during focused ion beam processing; and the step of performing position correction of the focused ion beam is performed at the initial times when starting up the focused ion beam processing step or switching from one form of focused ion beam processing to another form of focused ion beam processing, and the timing of subsequent position correction operations is calculated by adding a correction amount based on a current focused ion beam diameter to the time interval.

4. A focused ion beam processing method according to claim 3; wherein the step of calculating the timing of subsequent position correction operations by adding a correction amount based on a current focused ion beam diameter is performed such that a position correction time interval is shortened when a correction amount is larger than the beam diameter, and the position correction time interval is lengthened when the correction amount is smaller than the beam diameter.

5. A method of processing a sample using a focused ion beam, comprising:

a rough processing step of processing the sample using the focused ion beam at a first beam diameter;

a fine processing step of processing the sample using the focused ion beam at a second beam diameter smaller then the first beam diameter; and repeatedly performing position correction of the focused ion beam during the rough and fine processing steps, the time interval between successive position correction operations being dependent upon the beam diameter of the focused ion beam, such that position correction is performed at shorter intervals in the fine processing step than in the rough processing step.

6. A method of processing a sample using a focused ion beam according to claim 5; further comprising an intermediate processing step of processing the sample using the focused ion beam at a third beam diameter smaller than the first beam diameter and larger than the second beam diameter; wherein the step of position correction is performed at shorter intervals in the intermediate processing step than in the rough processing step and at larger intervals than in the fine processing step.

7. A method of processing a sample using a focused ion beam according to claim 6; wherein the intermediate processing step comprises the step of depositing a protective film on the sample, the rough processing step comprises the step of etching through the protective film and the sample surface to form a hole to expose cross-sectional structure of the sample, and the fine processing step comprises the steps of polishing the hole and observing the cross-sectional structure using the focused ion beam.

8. A method of processing a sample using a focused ion beam according to claim 5; further comprising the step of using the focused ion beam to observe the cross-sectional structure.

9. A method of processing a sample using a focused ion beam according to claim 5; wherein the step of performing position correction comprises the steps of using the focused ion beam to etch a marker on the sample at a location remote from where the cross section is to be formed, and repeatedly checking the position of the marker to determine deviation of the focused ion beam from a given position.

* * * * *